(12) United States Patent
Lichtblau

(10) Patent No.: US 9,327,047 B1
(45) Date of Patent: *May 3, 2016

(54) UVC AIR DECONTAMINATION SYSTEM

(71) Applicant: George J. Lichtblau, New Canaan, CT (US)

(72) Inventor: George J. Lichtblau, New Canaan, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/728,284

(22) Filed: Jun. 2, 2015

(51) Int. Cl.
A61L 9/20 (2006.01)

(52) U.S. Cl.
CPC .......................................... A61L 9/20 (2013.01)

(58) Field of Classification Search
CPC .......................................................... A61L 9/20
See application file for complete search history.

(56) References Cited

U.S. PATENT DOCUMENTS

| 4,017,736 | A | * | 4/1977 | Ross | F24F 3/16 |
| | | | | | 250/435 |
| 8,623,275 | B2 | | 1/2014 | Deshays | |
| 8,636,950 | B2 | | 1/2014 | Deshays | |
| 8,791,441 | B1 | * | 7/2014 | Lichtblau | A61L 2/10 |
| | | | | | 250/455.11 |
| 2006/0278075 | A1 | | 12/2006 | Blackner | |
| 2010/0044319 | A1 | * | 2/2010 | Engel | A61L 9/20 |
| | | | | | 210/746 |
| 2013/0336839 | A1 | * | 12/2013 | Gil | A61L 2/10 |
| | | | | | 422/24 |
| 2014/0030144 | A1 | * | 1/2014 | Krosney | A61L 9/20 |
| | | | | | 422/4 |

* cited by examiner

Primary Examiner — Jack Berman
Assistant Examiner — Eliza Osenbaugh-Stewar
(74) Attorney, Agent, or Firm — Preti Flaherty Beliveau & Pachios LLP

(57) ABSTRACT

A UVC radiation system for producing decontaminated air which flows into the surroundings of the system while blocking UVC radiation from entering the surrounding environment. In one embodiment, the system comprises a first housing forming a first air chamber and having multiple side walls each having one or more UVC lamps adjacent thereto. Each side wall has air vent openings in a pattern which confronts substantially the entire length of the one or more adjacent lamps. A second housing surrounds the first housing and lamps and forms a second air chamber having one or more walls containing an air filter to permit air to flow through the filter into the surrounding environment and to prevent UVC radiation from entering the environment.

28 Claims, 4 Drawing Sheets

UVC AIR DECONTAMINATION SYSTEM

STATEMENT REGARDING FEDERALLY SPONSORED RESEARCH OR DEVELOPMENT

N/A

CROSS REFERENCE TO RELATED APPLICATIONS

N/A

BACKGROUND OF THE INVENTION

An ultraviolet radiation system is described in U.S. Pat. No. 8,791,441 by the same inventor as the present invention which provides UVC radiation at a wavelength of 253.7 nm which is effective to kill or deactivate pathogens on surfaces irradiated by the emitted UVC radiation and simultaneously effective to decontaminate air which passes uniformly over the entire length of the UVC lamps. Uniformly flowing air cools the lamps to maximize the conversion efficiency of the power input to the lamps to UVC radiation from the lamps, and at the same time decontaminates the flowing air such that air in the room is also decontaminated. UVC radiation is harmful to persons and therefore an ultraviolet radiation system such as described in the aforementioned patent are not intended to be operated with people present in the vicinity of the emitted radiation.

It would be beneficial to have a UVC radiation system which provides the intended decontamination of air in a room or other facility in which the system is placed and which can be operated in the presence of people.

BRIEF SUMMARY OF THE INVENTION

The present invention provides a UVC radiation system which produces decontaminated air caused to flow into surrounding air of the system but does not permit the UVC radiation to pass out of the system. In one embodiment the system comprises a first housing forming a first air chamber and having multiple side walls each having one or more UVC lamps adjacent to respective side walls. Each side wall has air vent openings in a pattern which confronts substantially the entire length of the at least one adjacent lamps. A second housing surrounds the first housing and lamps and forms a second air chamber having one or more walls each containing an air filter to permit air to flow through the filter into the surrounding atmosphere and to not permit UVC radiation to pass through the filter. A fan is in fluid coupling relationship with the first housing and causes air to flow into the first housing and out through the pattern of vent openings in each side wall and across substantially the entire length of the one or more lamps adjacent each side wall into the second air chamber which surrounds the first air chamber. The flowing air from the second air chamber flows through the one or more filters into the surrounding atmosphere to thereby provide decontaminated air in the surrounding atmosphere. UVC radiation does not pass through the one or more filters and therefore it is safe for people to be present in the surrounding atmosphere without exposure to UVC radiation. Operation of the system is governed by an electronic controller which typically includes a microprocessor based controller and associated controls, indicators and displays for the system. The controller is operative to monitor the electrical current to one or more electronic ballasts which drive the lamps and to shut down the system in the event that the current is below a reference level. In this manner the system operates at an optimum level for most effective UVC radiation from the one or more lamps.

BRIEF DESCRIPTION OF THE SEVERAL VIEWS OF THE DRAWINGS

The invention will be more fully described in the following detailed description in conjunction with the drawings, in which.

DETAILED DESCRIPTION OF THE INVENTION

The content of U.S. Pat. No. 8,791,441 entitled Ultraviolet Radiation System is herein incorporated by reference in its entirety for all purposes.

Figure 1:
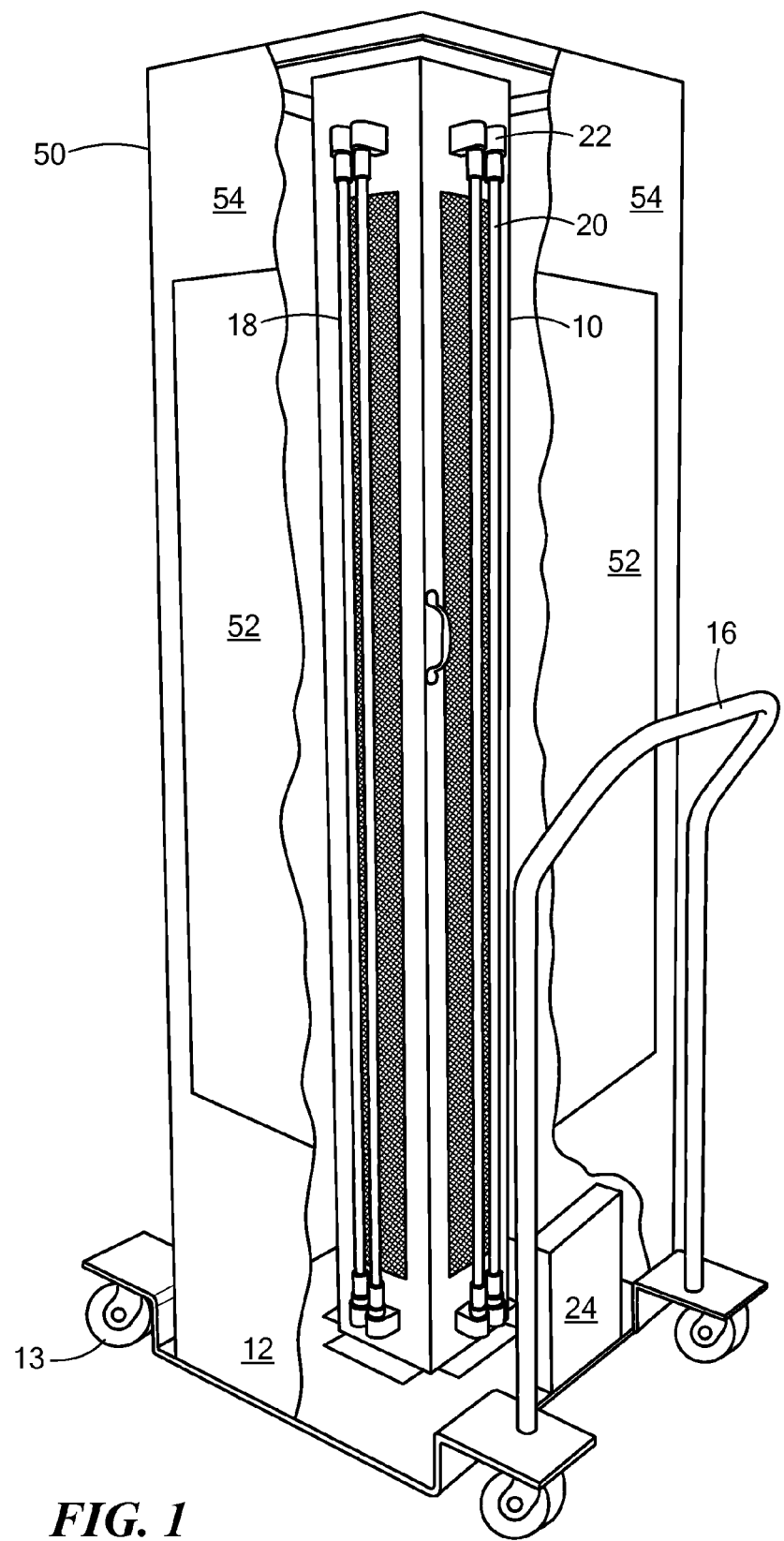
FIG. 1 is a pictorial view of one embodiment of the UVC air decontamination system in accordance with the invention.

One embodiment of an ultraviolet radiation system in accordance with the invention is illustrated in FIG. 1. A square enclosure or housing 10 is supported on a wheeled base or dolly 12 having four wheels or casters 13 positioned at corners of the base as shown. A handle 16 may be positioned on a side of the base as shown for ease of movement of the system The enclosure 10 has air vent openings 18 through each side wall of the enclosure as described below. One or more UVC lamps 20 are disposed at each side wall of the enclosure 10 and are electrically and mechanically mounted to the enclosure by connectors 22. The lamps are typically low pressure, high power mercury or amalgam vapor lamps which radiate UVC radiation. The one or more lamps at each side wall of the enclosure confront the vent openings in the respective side walls of the enclosure which pattern of openings are substantially coextensive with the length of the lamps. An outer enclosure or housing 50 surrounds housing 10 and lamps 20. The housing 50 is fabricated of aluminum or other material which will block the UVC radiation from the lamps.

Figure 2:
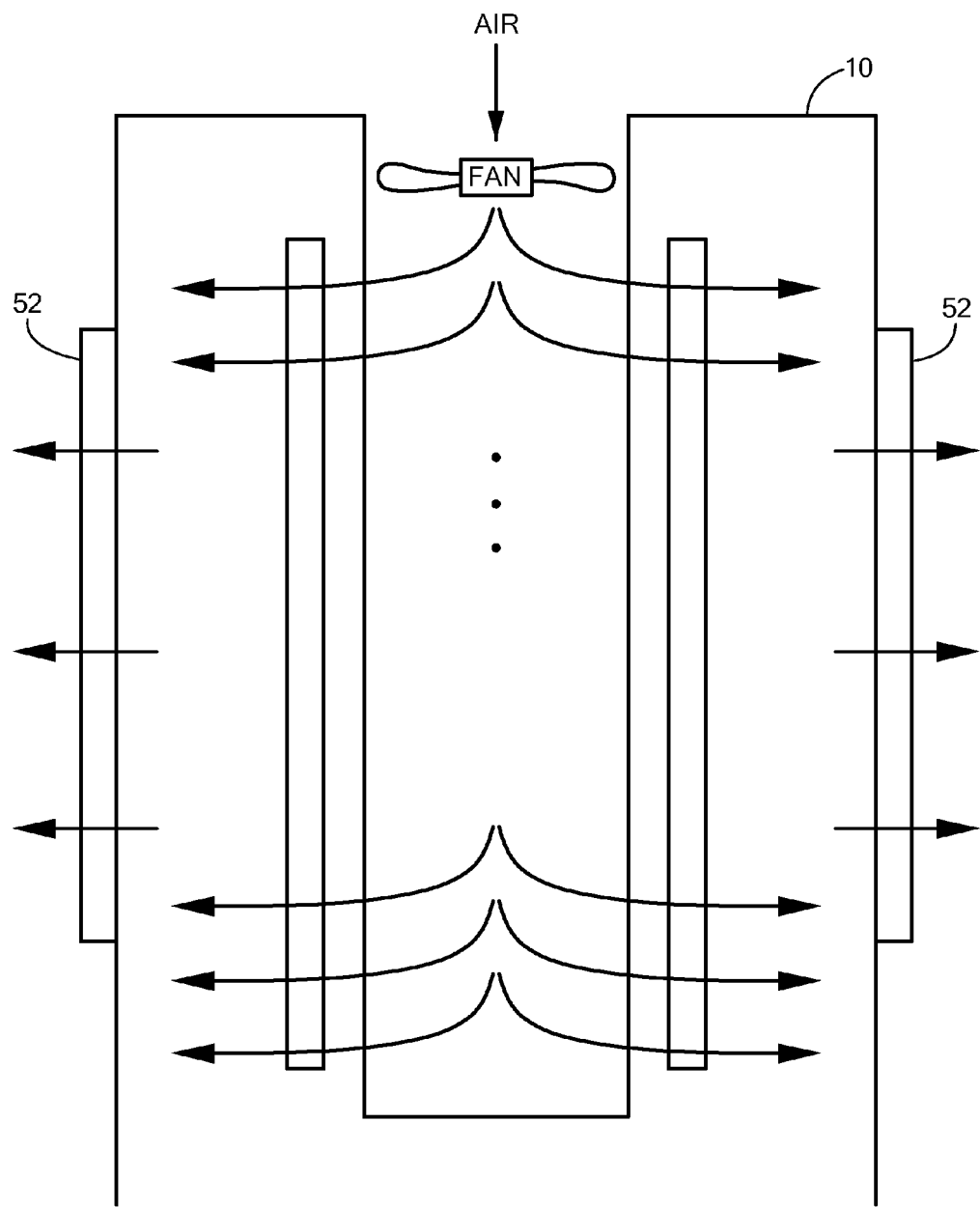
FIG. 2 is a diagrammatic elevation view of the embodiment of FIG. 1 illustrating the air flow.
Figure 3:
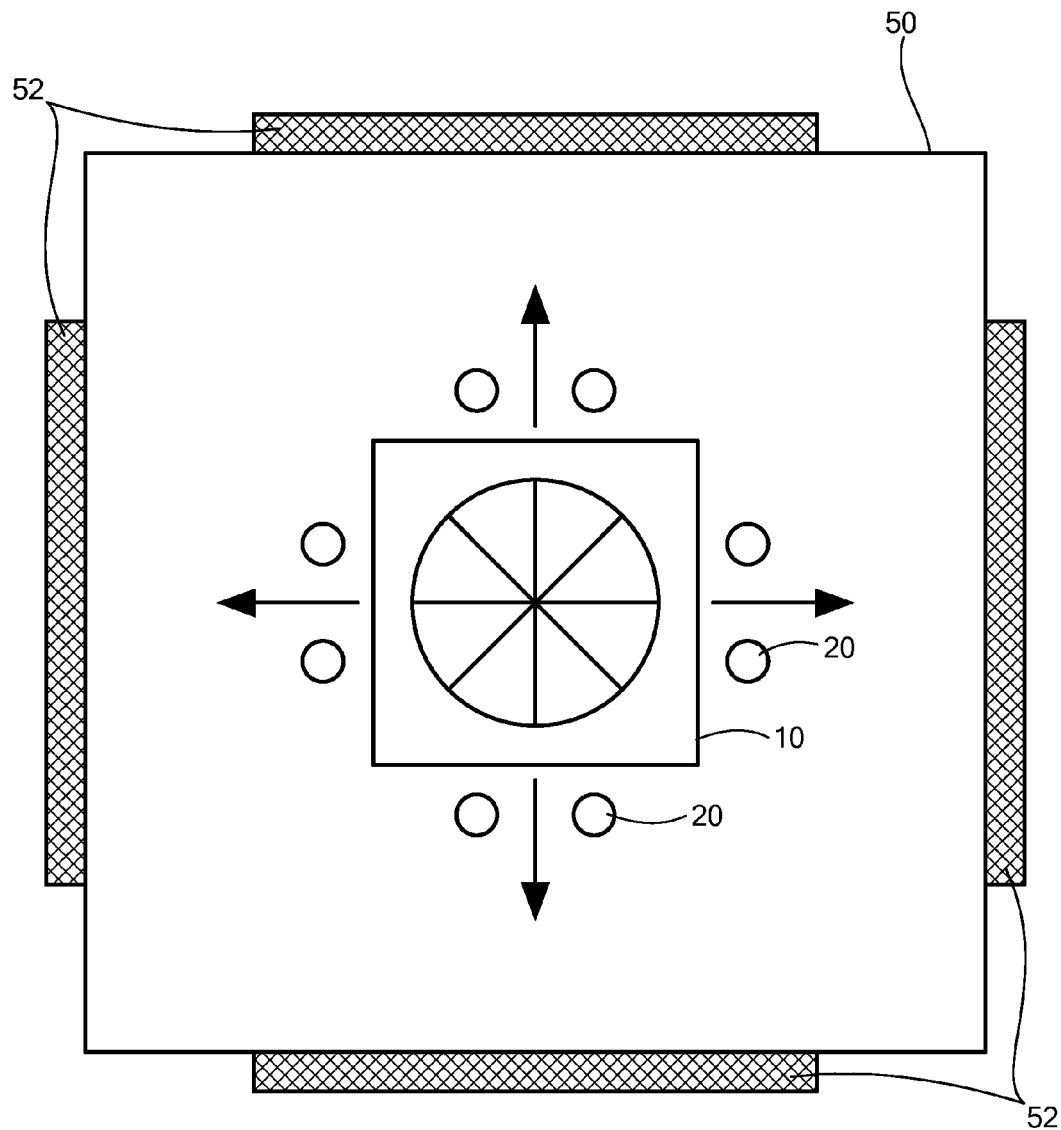
FIG. 3 is a diagrammatic top view of an embodiment of the invention.

An air filter, preferable a HEPA filter 52 is disposed in an opening on each side wall 54 of housing 50. The filter passes air but does not pass UVC radiation. Filters 52 typically have a frame supporting the HEPA filter media and the filter frame can be mounted in tracks or channels formed in the side walls. In other embodiments, a filter 52 may be in less than all the side walls, or multiple filters may be located in a single or multiple side walls. A fan or blower, not visible in FIG. 1, is mounted at the upper end of the enclosure 10 and is operative to direct an air stream downward through the enclosure. The air stream is vented through the openings 18 and thence across the lamps 20 to provide cooling of the lamps substantially along their entire length, as illustrated schematically in FIG. 2. The air flow is sufficient to maintain the operating temperature of the lamps at a level to achieve UVC radiation from the lamps at their maximum rated capacity. The lamps are arranged around the housing to provide 360° decontaminated air flow into the room in which the system is operating. Electronic ballasts for the UVC lamps are typically located inside the enclosure 10. Electronic controls are mounted in a housing 24 or control panel which can be mounted on the base 12 or on handle 16 or other convenient location. The controls may include a timer which is adjustable to determine the operating time for an air decontamination cycle of the system.

One or more of the sides of the enclosures 10 and 50 can be hinged or otherwise openable for access to the interior such as for maintenance and repair of components located within the enclosures.

The lamps are typically enclosed within a sleeve of protective material, which is UVC transmissive, such as Teflon (polytetrafluoroethylene), to avoid shattering of the lamp envelope if the lamp is struck by an object or mishandled.

In one implementation, the housing 10 is about 66 inches in height and about 12 inches square. The lamps are, for example, model GH01554T5L5L or similar mercury vapor lamps having a height of 60.5 inches. Such lamps are manufactured by Light-Sources, Inc. among others. The fan is a six inch muffin fan having an a typical flow capacity of 250 ft$^3$/min, and can be, for example, a model A1606V1H made by Sofasco International. The lamp temperature is maintained substantially at its optimum operating temperature to maximize the radiation output. The output is typically about 250% higher than that achieved by uncooled mercury germicidal lamps.

Figure 4:
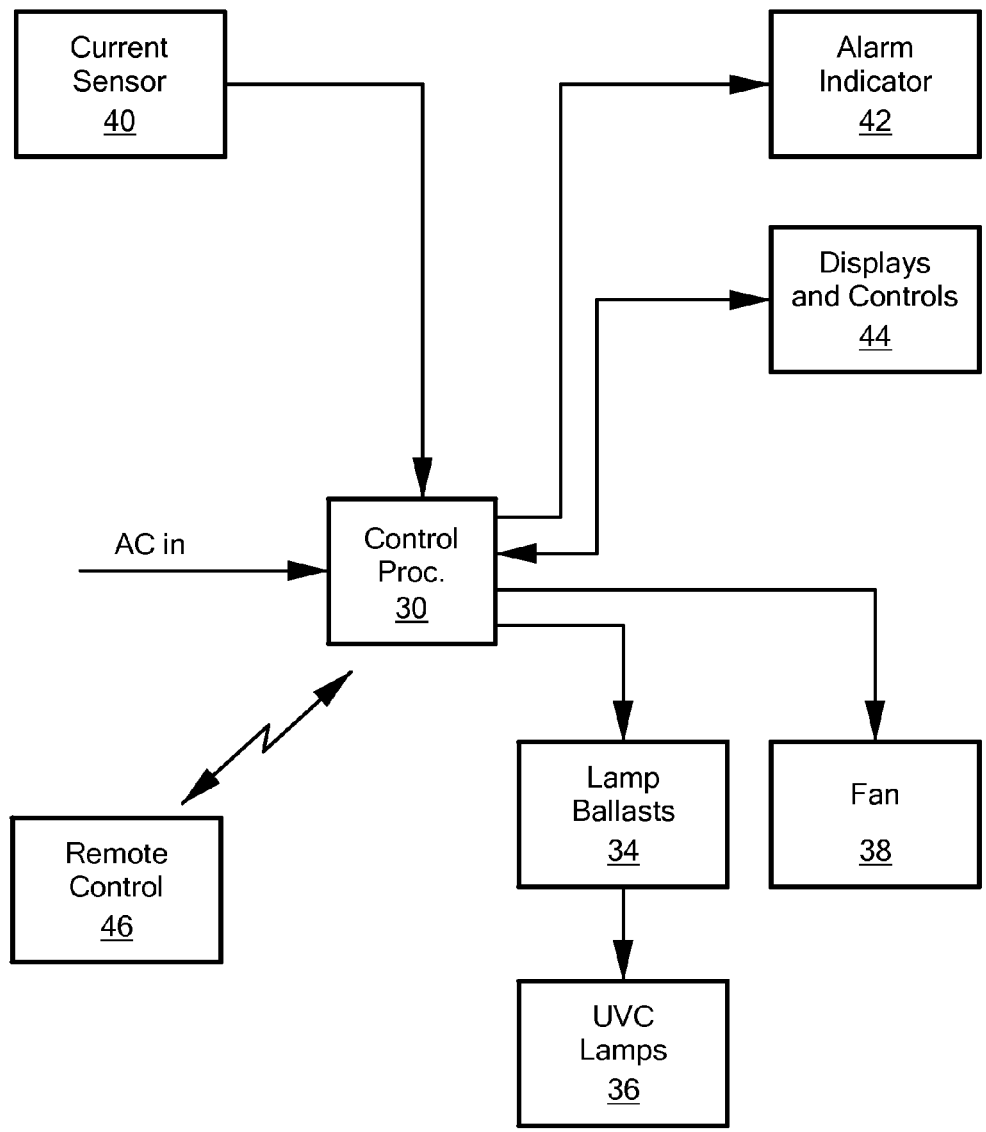
FIG. 4 is a block diagram of the system.

The system 13 illustrated in block diagram form in FIG. 4. AC input power is applied to a control processor 30. The input power is typically from a standard 120 or 220/240 AC volt outlet. The processor 30 is coupled to displays and controls 44 which include indicators or displays of system conditions and controls for system operation. The display may have a two digit electronic display to indicate the time remaining in a decontamination cycle. The processor drives the lamp ballasts 34 which in turn drive the UVC lamps 36. The ballasts are preferably electronic ballasts. The processor also controls a fan 38 for lamp cooling. One or more current sensors 40 are associated with each lamp to sense if the lamps are operating properly and to provide a signal to the processor 30 in the event that the sensed current falls below a predetermined threshold level. This could occur for example in the event of a lamp failure. The power control processor in response to such signal from the sensor provides a signal to an alarm indicator 42 which can provide a visual, audible or other indicator of a fault condition. The alarm indicator may be Sonalert audible annunciator. The alarm indicator may be included in the displays/controls unit 44. The control processor can also be operative in response to a signal from the sensor 40 to shut down the system. The shutdown may also be signified by a suitable alarm indication which may be a visual or audible alarm or an error message appearing on a system display. It will be appreciated that the degree of current monitoring can vary to suit particular system implementations.

A remote control 46 may be employed in wireless communication with the processor 30 for remote operation of the system. The remote control typically employs an RF or infrared link and has operating controls and indicators for operating the system inside or outside of the site being irradiated.

It will be appreciated that the invention is not to be limited by the particular embodiments shown and that modifications and alternative implementations are contemplated and within the intended scope of the invention. For example, the fan or blower can be disposed at the bottom of the first air chamber or other position therein to accomplish intended air flow. The number and type of UVC lamps and filters can vary to suit intended radiation output and coverage. The physical configuration of the system may also be of many different forms. Accordingly, the invention is not to be limited by what has been particularly shown and described except as defined by the appended claims.

The invention claimed is:

1. An ultraviolet air decontamination system comprising:
  a plurality of UVC lamps providing UVC radiation
  a first housing forming a first air chamber and having multiple side walls, each side wall being adjacent to at least one or the plurality of lamps, and each side wall having air vent openings in a pattern which confront substantially the entire length of the at least one adjacent lamps;
  the plurality of UVC lamps and the air first air chamber arranged in a vertical orientation;
  the at least one lamp adjacent each side of the side walls being positioned adjacent the pattern of air vent openings in that side wall;
  a second housing surrounding said first housing and forming a second air chamber and having at least one wall containing an air filter to permit air to flow through the air filter and not permit UVC radiation to pass through the filter;
  a fan in fluid coupling relationship with the first housing to cause air to flow from the surrounding atmosphere into said first housing and out through the pattern of vent openings in each side wall and across substantially the entire length of the at least one of the plurality of lamps adjacent each side wall into the second air chamber surrounding said first air chamber;
  the UVC radiation being effective to kill pathogens in the air of the atmosphere of the second air chamber;
  the flowing air being effective to cool the plurality of lamps to an optimum operating temperature to maximize the UVC radiation output from the plurality of UVC lamps;
  a power source including one or more electronic ballasts for energizing the one or more lamps and fan; and
  an electronic controller to control the operation of the system including the time of an air decontamination cycle and the monitoring of current to the one or more electronic ballasts.

2. The system of claim 1 wherein said filter is a HEPA filter.

3. The system of claim 1 wherein the second housing has multiple side walls each of which contain an air filter which permits air to flow through the air filter and not permit UVC radiation to pass through the filter.

4. The system of claim 3 wherein the first and second housings have the same number of side walls.

5. The system in claim 1 wherein the fan is located at the top of the first air chamber.

6. The system of claim 1 where the fan is located at the bottom of the air chamber.

7. The system of claim 1 wherein the fan is a muffin fan.

8. The system of claim 1 wherein the first housing has side walls which are reflective to UVC radiation.

9. The system in claim 8 wherein the first housing is aluminum.

10. The system of claim 9 wherein the side walls are oxidized to be reflective to UVC radiation.

11. The system of claim 1 wherein one or more lamps are low pressure, high output mercury lamps.

12. The system of claim 1 wherein one or more lamps are low pressure, high output, amalgam lamps.

13. The system of claim 1 wherein the first housing has four side walls and two lamps disposed at each side wall.

14. The system of claim 1 wherein the first housing has four side walls and one lamp is disposed at each side wall.

15. The system of claim 1 wherein the at least one ballast is located in said first air chamber.

16. The system of claim 1 wherein the first and second housings are supported on a moveable dolly.

17. The system of claim 1 wherein the air flowing across the one or more lamps increases the UVC lamp output at least two times the output of uncooled one or more lamps.

18. The system of claim 1 including a control panel having an electronic display.

19. The system of claim 18 where in the display is a two digit electronic display to indicate the time remaining in a decontamination cycle.

20. The system of claim 1 including an annunciator to indicate the end of a decontamination cycle.

21. The system of claim 20 wherein the annunciator is an audible indicator.

22. The system of claim 1 including a timer coupled to the power source and adjustable to set an operating time for the system.

23. The system of claim 1 wherein each one or more lamps is enclosed in a protective sleeve of UVC transmissive material.

24. The system of claim 23 wherein the protective sleeve is made of polytetrafluoroethylene.

25. The system of claim 1 wherein the controller is operative to turn off the UVC lamps in the event that the current to the ballasts is less than a reference level, and to display an error message on the display.

26. The system of claim 1 wherein the electronic ballasts operate from 120 AC volts.

27. The system of claim 1 wherein the electronic ballasts operate at 220/240 AC volts.

28. The system of claim 1 wherein the control panel includes a push-button switch to start or stop a decontamination cycle.

* * * * *